US007189811B2

(12) United States Patent
Panda et al.

(10) Patent No.: US 7,189,811 B2
(45) Date of Patent: Mar. 13, 2007

(54) PROCESS FOR SOLUBILIZATION OF RECOMBINANT PROTEINS EXPRESSED AS INCLUSION BODY

(75) Inventors: Amulya Kumar Panda, New Delhi (IN); Mohammed Gulebahar Sheikh, New Delhi (IN); Addala Naga Sai Eshwari, New Delhi (IN); Lalit Chander Garg, New Delhi (IN)

(73) Assignee: National Institute of Immunology (IN)

( * ) Notice: Subject to any disclaimer, the term of this patent is extended or adjusted under 35 U.S.C. 154(b) by 110 days.

(21) Appl. No.: 10/655,664

(22) Filed: Sep. 5, 2003

(65) Prior Publication Data
US 2004/0235089 A1    Nov. 25, 2004

(30) Foreign Application Priority Data
Sep. 6, 2002    (IN)    ............................. 912/DEL/02

(51) Int. Cl.
*C07K 1/00*    (2006.01)
(52) U.S. Cl. ..................................... 530/350
(58) Field of Classification Search ............... 530/350; 514/12
See application file for complete search history.

(56) References Cited
U.S. PATENT DOCUMENTS
5,663,304 A *    9/1997    Builder et al. .............. 530/399

OTHER PUBLICATIONS

Lindwall et al., A sparse matrix approach to the solubilization of overexpressed proteins, Protein Engineering (2000), 13(1), p. 67-71.*
J. F. Kane and D. L. Hartley, "Formation of recombinant protein inclusion bodies in *Echerichia coli*," May 1998, pp. 95-101, Tibtech [vol. 6].
A. Mirtraki and J. King, "Protein Folding Intermediates and Inclusion Body Formation," Jul. 1989, pp. 690-697, Bio/Technology [vol. 7].
C. H. Schein, "Protein of Soluble Recombinant Proteins in Bateria," Nov. 1989, pp. 1141-1149, Bio/Technology [vol. 7].
B. Fischer, I. Summer and P. Goodenough, "Isolation, Renaturation and Formation of Disulfide Bonds of Eukaryotic Proteins Expressed in *Escherichia coli* as Inclusion Bodies," Jan. 5, 1993, pp. 3-13, Biotechnology and Bioengineering [vol. 41].
R. Rudolph and H. Lilie, "In vitro folding of inclusion body proteins," Jan. 1996, pp. 49-56, The FASEB Journal [vol. 10].
J. Stockel, K. Doring, J. Malotka, F. Jahnig, and K. Dornmair, "Pathway of detergent-mediated and peptide ligand-mediated refolding of heterodimeric class II major histocompatibility complex (MHC) molecules," 1997, pp. 684-691, Eur. J. Biochem. [vol. 248].
M. Cardamone, N. K. Puri and M. R. Brandon, "Comparing the Refolding and Reoxidation of Recombinant Porcine Growth Hormone from a Urea Denatured State and from *Escherichia coli* Inclusion Bodies," 1995, pp. 5773-5794, American Chemical Society [vol. 34].
R. R. Burgess, "Purification of Overproduced *Escherichia coli* RNA Polymerase σ Factors by Solubilizing Inclusion Bodies and Refolding from Sarkosyl," 1996, pp. 145-149, Methods in Enzymology [vol. 273].
R. Randolph, G. Bohm, H. Lilie and R. Jaenicke, "Folding proteins," pp. 57-89.
E. De Bernardez Clark, E. Schwarz and R. Rudolph, "Inhibition of Aggregation Side Reactions during in Vitro Protein Folding," 1999, pp. 217-255, Academic Press.
T. M. Przybycien, J. P. Dunn, P. Valax and G. Georgiou, "Secondary structure characterization of β-lactamase inclusion bodies," 1994, pp. 131-136, Protein Engineering [vol. 7 No. 1].
G. A. Bowden, A. M. Paredes and George Georgiou, "Structure and Morphology of Protein Inclusion Bodies in *Escherichia coli*," Aug. 1991, pgs., Bio/Technology [vol. 9].
M. A. Speed, D. I. C. Wang and J. King, "Specific aggregation of partially folded polypeptide chains: The molecular basis of inclusion body composition," Oct. 1996, Nature Biotechnology [vol. 14].
M. M. Carrio, A. Villaverde, "Protein aggregation as bacterial inclusion bodies is reversible," 2001, pp. 29-33, FEBS Letters [vol. 489].
R. Cubarsi, M. M. Carrio, A. Villaverde, "In Situ Proteolytic Digestion of Inclusion Body Polypeptides Occurs as a Cascade Process," Feb. 12, 2001, pp. 436-441, Biochemical and Biophysical Research Communications [vol. 282], doi:10.006/bbrc.2001.4583, available online at http://www.idealibrary.com.
A. K. Patra, R. Mukhopadhyay, R. Mukhija, A. Krishnan, L. C. Garg and A. K. Panda, "Optimization of Inclusion Body Solubilization and Renaturation of Recombinant Human Growth Hormone from *Escherichia coli*," Nov. 10, 1999, pp. 182-192, Protein Expression and Purification [vol. 18], doi:10,1006/prep.1999. available online at http://www.idealibrary.com.
R. J. St. John, J. F. Carpenter and T. W. Randolph, "High pressure fosters protein refolding from aggregates at high concentrations," Nov. 9, 1999, PNAS [vol. 96, No. 23].
O. G. P. Isaksson, S. Eden and J. O. Jansson, "Mode of Action of Pituitary Growth Hormone on Target Cells," 1985, pp. 483-499, Ann. Rev. Physiol.
R. K. Chawla, Ph.D., J. S. Parks, M.D. and D. Rudman, M.D., "Structural Variants of Human Growth Hormone: Biochemical, Genetic, and Clinical Aspects," 1983, pp. 519-547, Ann. Rev. Med. [vol. 34].

(Continued)

*Primary Examiner*—Robert A. Wax
*Assistant Examiner*—Agnes B. Rooke
(74) *Attorney, Agent, or Firm*—Renner, Otto, Boisselle & Sklar, LLP

(57) ABSTRACT

The present invention relates to the solubilization and recovery in high yield, of inclusion body proteins from host cells using an appropriate denaturating agent. The process avoids the use of high concentration of chaotropic agents such as guanidine hydrochloride or urea.

10 Claims, 3 Drawing Sheets

OTHER PUBLICATIONS

Figure 1A:
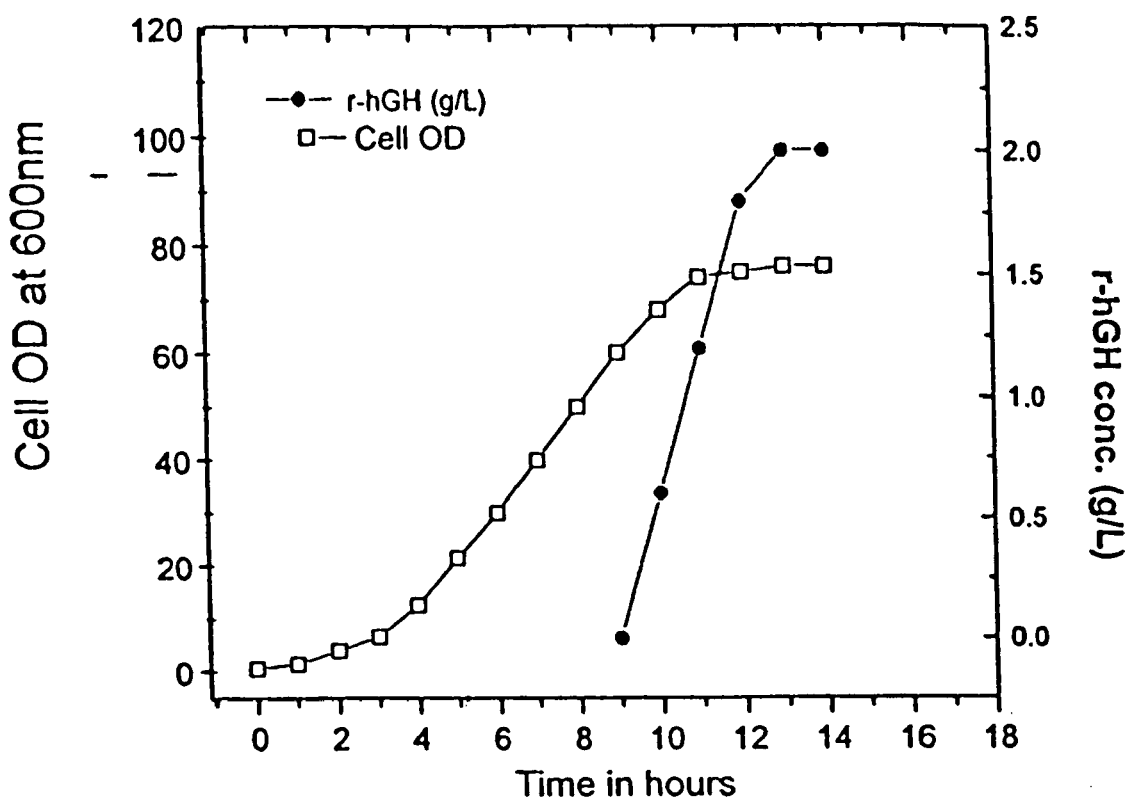

R. Mukhija, P. Rupa, D. Pillai and L. C. Garg, "High-level production and one-step purification of biologically active human growth hormone in *Escherichia coli*," 1995, pp. 303-306, Gene. [vol. 165].

N. Shin, D Kim, C Shin, M. Hong, J. Lee and H. Shin, "High-Level production of human growth hormone in *Escherichia coli* by a simple recombinant process," 1998, pp. 143-151, Journal of Biotechnology [vol. 62].

H. Mori, T. Yano, T. Kobayashi and S. Shimizu, "High Density Cultivation of Biomass in Fed-Batch System with Do-Stat," 1979, pp. 313-319, Journal of Medical Engineering of Japan [vol. 12, No. 4].

A. K. Panda, R. H. Khan, K. B. C. Appa Rao and S. M. Totey, "Kinetics of inclusion body production in batch and high cell density fed-batch culture of *Escherichia coli* expressing ovine growth hormone," 1999, pp. 161-172, Journal of Biotechnology [vol. 75].

A. Mitraki, C. Haase-Pettingell, and J. King, Mechanisms of Inclusion Body Formation, "Mechanisms of Inclusion Body Formation," 1981, pp. 35-49, Protein Refolding, Chapter 3.

* cited by examiner

PROCESS FOR SOLUBILIZATION OF RECOMBINANT PROTEINS EXPRESSED AS INCLUSION BODY

RELATED FOREIGN APPLICATIONS

This application claims priority to Indian Application Number 912/Del/2002 filed on Sep. 6, 2002. The previously filed foreign application is hereby incorporated by reference in its entirety.

FIELD OF THE INVENTION

The present invention relates to the solubilization and recovery in high yield, of inclusion body proteins from host cells using an appropriate denaturating agent. The process avoids the use of high concentration of chaotropic agents.

BACKGROUND AND PRIOR ART

High level expression of recombinant proteins in host cells such as E. coli often leads to accumulation of proteins as insoluble aggregates in vivo as inclusion bodies. Inclusion bodies are dense aggregates of misfolded polypeptides devoid of bioactivity that need elaborate solubilization/refolding protocols to achieve a native conformation. The formation of inclusion bodies is mainly attributed to the over-expression of proteins in a cell lacking required accessories for its folding to native form. Endogenous proteins when over-expressed also accumulate as inclusion bodies. There is no direct correlation between the propensity of the inclusion body formation of a certain protein and its intrinsic properties, such as molecular weight, hydrophobicity, folding pathways and so on. In case of proteins having disulfide bonds, formation of protein aggregates as inclusion bodies is anticipated since the reducing environment of bacterial cytosol inhibits the liberation of disulfide bonds. It is desirable to recover these proteins from the cells for maximum recovery of bioactive proteins.

Proteins expressed as inclusion bodies are currently solubilized by the use of high concentration of chaotropic agents such as urea, guanidine hydrochloride, and thiocyanate salts, detergents such as SDS, N-cetyl trimethyl ammonium chloride, and sarkosyl (sodium N-lauroyl sarcosine). The soluble denatured proteins are then refolded to their native state after removing the chaotropic agents or other salts by dialyzing the proteins in buffers containing reducing and oxidizing agents. Renaturation of recombinant proteins from inclusion bodies into bioactive form is cumbersome, results in low recovery of the final product and also accounts for the major cost in overall production of recombinant proteins. However in the case where simple high yielding protein refolding process is developed for the aggregated recombinant proteins, high level expression of proteins as inclusion body provides a straightforward strategy for the cost-effective production of therapeutic proteins. Significant features of protein aggregates in inclusion bodies are the existence of native-like secondary structure of the expressed protein and their resistance to proteolytic degradation. The aggregation leading to inclusion body formation has also been reported to be due to specific intermolecular interaction among a single type of protein molecules. The formation of inclusion bodies thus facilitates the easy isolation and recovery of the expressed proteins in denatured form. Loss during recovery of protein from inclusion bodies is compensated by high initial level of expression.

It has also been reported that protein aggregation in inclusion bodies is a reversible process and inclusion bodies are resistant to proteolytic degradation and peptide degradation process by enzymes occurs as a cascade in situ. Solubilization profile of inclusion bodies in different buffers gives an idea about the dominant forces involved in protein aggregates during high level expression of recombinant protein as inclusion bodies. Such information can thus be exploited to develop mild solubilizing buffer, which will protect the native-like secondary structure of the protein during solubilization. Presence of other contaminating proteins has negative effect on overall yield of the bioactive protein during refolding of denatured protein. As aggregation is the major factor responsible for the reduced yield of bioactive protein from the inclusion bodies, it is desirable to develop soluilization process which does not unfold the protein completely.

Some workers have tried to increase the overall yield of purified bioactive proteins from the inclusion bodies by trying to protect the existing secondary structure of the proteins during solubilization and the refolding is carried out in such a way that interaction between partially folded polypeptide intermediates is minimized. This is achieved using detergents, high pH, use of high pressure for solubilization of protein aggregates. However all these above methods have their inherent disadvantages. High pH treatment sometimes tends to denature the proteins, it is difficult to remove the detergents after solubilization and high pressure does not completely solubilize the protein aggregates. Most of the time, the aggregation leading to inclusion body formation is predominantly due to hydrophobic interaction and due to mixed disulfide bond formation.

It would be ideal if the solubilizing agent has the ability of disrupting both hydrophobic interaction and disulfide bond formation resulting in solubilization of the inclusion body protein. Having worked on this line for long, the Applicant has developed a novel process that uses a novel denaturating solution for solubilization and recovery of inclusion body proteins in high yield from host cells.

OBJECTS OF THE INVENTION

The main object of the invention is to provide a process for solubilization of proteins expressed as inclusion bodies in host cells using a denaturating solution of a mercapto-organic solvent and urea.

Another object is to provide a process that avoids the use of high concentration of chaotropic agents.

Yet another object is to provide a process whereby proteins in their bioactive form are recovered in high yield by balancing the ingredients of the denaturing solution.

DETAILED DESCRIPTION OF THE INVENTION

Accordingly, the invention provides a novel process for solubilization and recovery of bioactive proteins from host cells, the process comprising:— providing a source of a host cell incorporating an insoluble synthesized or expressed protein in the form of an inclusion body, isolating and treating the inclusion body with a denaturating solution consisting of a mercapto-organic solvent at a concentration of 6–8 M and urea at a concentration of 1–2 M to solubilize the inclusion body and obtain solubilized protein, and refolding the solubilized protein by treatment with a refolding buffer to obtain a protein in its bioactive form.

Preferably, the process of the invention involves culturing host cells expressing recombinant protein as as an inclusion body, extracting and isolating the inclusion body from the host cell into a denaturating solution consisting of a high concentration of mercapto-organic solvent and low concentration of urea to solubilize the protein and recovering the solubilized protein by conventional methods. The process may be effected at room temperature of about 25 to 35° C. at a pH of about 6–8 depending on the protein being used.

The process of the invention is generally applicable to the solubilization and recovery of proteins expressed as inclusion bodies and cytoplasmic aggregates in eukaryotic or prokaryotic cells. Examples of such proteins are growth hormones, interferons, interleukins, immunogens, lymphokines and so on. The growth hormones may be hGH, pGH, bGH, fMD etc. Such proteins may be expressed as inclusion bodies or cytoplasmic aggregates in any prokaryotic cell such as *E. coli*, bacteria and yeasts as well as in any eukaryotic cell.

Preferably, the aggregates of proteins or inclusion bodies, as they are called, may be solubilized by treatment with a denaturating solution consisting of a mercapto-organic solvent and urea. The mercapto-organic solvent may be a hydrosulphide of an alcohol such as mercaptoethanol [$C_2H_5SH$] or mercaptobutanol [$C_4H_9SH$]. The most preferred solvent is β-mercaptoethanol. Urea or analogues of urea may preferably be used in the denaturating solution. The ratio of the mercapto-organic solvent to urea may be 3:1. Preferably, the concentration of the mercapto-organic solvent may be 6–8 M, while the concentration of urea may be as low as possible, may be 1–2 M.

The protein so solubilized may be refolded to its native conformation by treatment with a refolding buffer such as Tris buffer containing EDTA, sucrose, urea and glycerol.

Bioactive proteins recovered by the method of the invention is much higher as compared to prior art processes. The overall recovery of the bioactive protein from the denatured aggregate is around 50 to 60%.

It is hypothetised that high concentration of the mercapto-organic compound in combination with low concentration of urea would assist in disrupting the disulphide bonds and hydrophobic interaction of the proteins and solubilize them. Once the proteins are solubilized thus using this combination, they may be refolded into their bioactive form in a refolding buffer environment. In the prior art, many workers have attempted use of low concentrations of mercaptoethanol for refolding of proteins after solubilization. [J. Biol Chem 1990 Feb. 15: 265(5); 2576–83—"Stable intermediates can be trapped during reversible refolding of urea"; Sheng Wu Hua Xue Yu Sheng Wu Wu Li Xue Bao (Shanghai) "Unfolding of Recombinant Single-chain Insulin in Denaturants containing Thiol Rea Guo Z Y, Qiao Z S, Feng Y M", 2001; 33(4):431–436; Protein Expr Purif: "Refolding and chracterization of a yeast dehydrodolichyl diphosphate synthase over *Escherichia coli.*", 2001 December; 23(3): 432–9; and J. Biochem (Tokyo): "Efficient folding of the insect neuropeptide eclosion hormone by protein disulfide isor", 2001 November; 130(5): 575–80]. High concentration of urea and very low concentration mercaptoethanol (10–20 mM) has been extensively used for the solubilization of inclusion body protein. However, none of them use high concentration β-mercaptoethanol along with low concentration of urea for inclusion body solubilization. This unique combination helps in solubilization of inclusion body protein aggregates without completely unfolding the proteins thus help in high recovery in bioactive form. Further, protein solubilization and recovery is a delicate process wherein even a slight shift or change in the reaction in concentration of a compound could affect the protein/inclusion body solubilization and recovery drastically. After several trials and experiments, the Applicant has found that high concentration of a mercapto-organic compound in combination with low concentration of urea gives high yield of proteins, all of which are found in their bioactive form. This is a surprising result, which is not expected and cannot be gleaned from the prior art. The recovery of proteins by the method of the invention is about 50–60%, whereas the prior art recovered only 10–20% of the solubilized proteins in their bioactive form.

The invention is described in detail with the aid of following examples, accompanying drawings. Various modification that may be apparent to one in the art are intended to fall within the scope of this invention.

DESCRIPTION OF THE ACCOMPANYING DRAWINGS

FIG. 1A: shows fermentation profile for the expression of r-hGH from *E. coli*

Figure 1B:
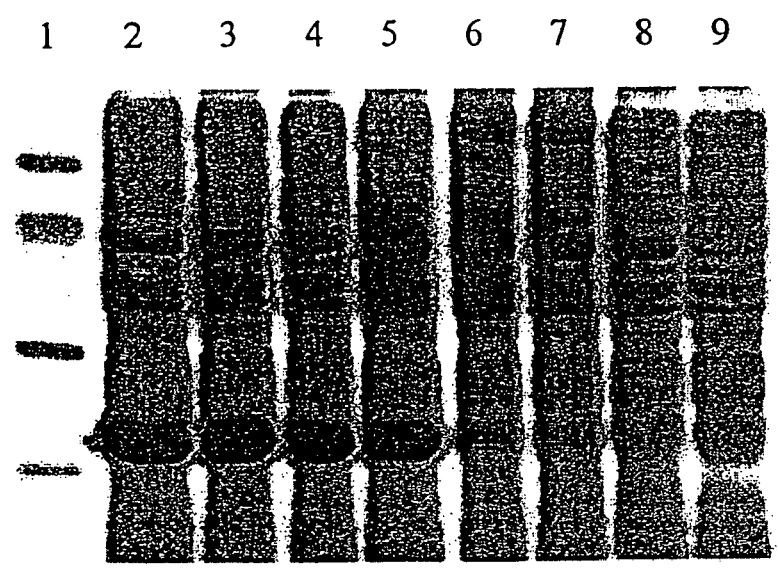

FIG. 1B: shows SDS-PAGE analysis of r-hGH expression Lane 1. Mol Wt marker, Lanes 2–5, induced samples, Lanes 6–8 uninduced cell samples from 0–4 hours of growth.

Figure 2:
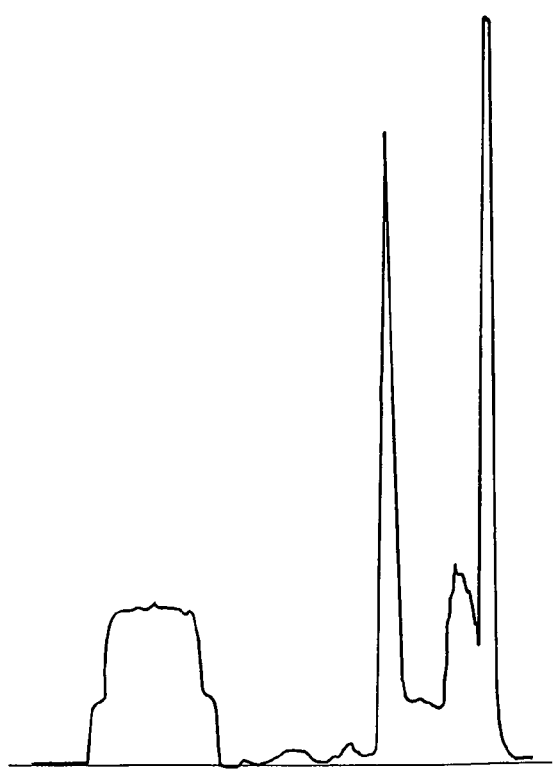

FIG. 2: shows Ion Exchange chromatoGram—Column parameters: Quaternary Ammonium-Sepharose column, Bed volume 40 ml, Load—120 ml, Flow rate—2 ml/min, chart speed—0.2 mm/min, sensitivity—0.2.

Figure 3:

FIG. 3: shows SDS-PAGE analysis of r-hGH purification using q-sepharose purification. Lane 1—Protein Load, Lane 2—Low Mol. Wt marker, Lane 3—Flow through, Lane 4—Wash, Lanes 5–7—Elute fractions of Peak 1, Lanes 8–9—Elute fractions of Peak 2.

Figure 4:
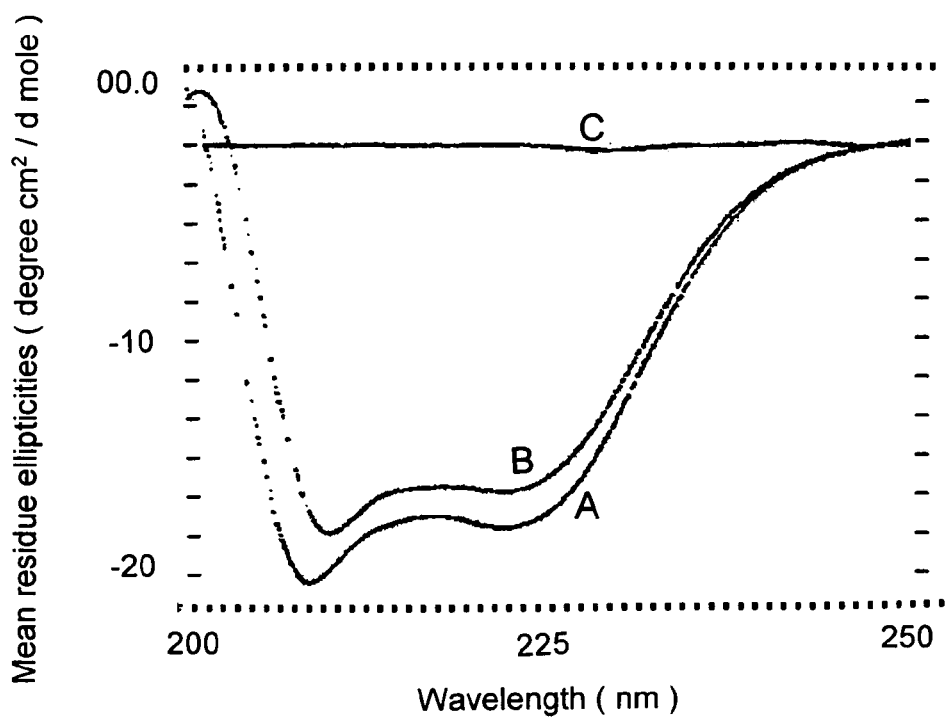

FIG. 4: shows CD spectra of the refolded r-hGH. A and B are the CD spectra of refolded r-hGH which is similar to that of native hGH.

Figure 5:
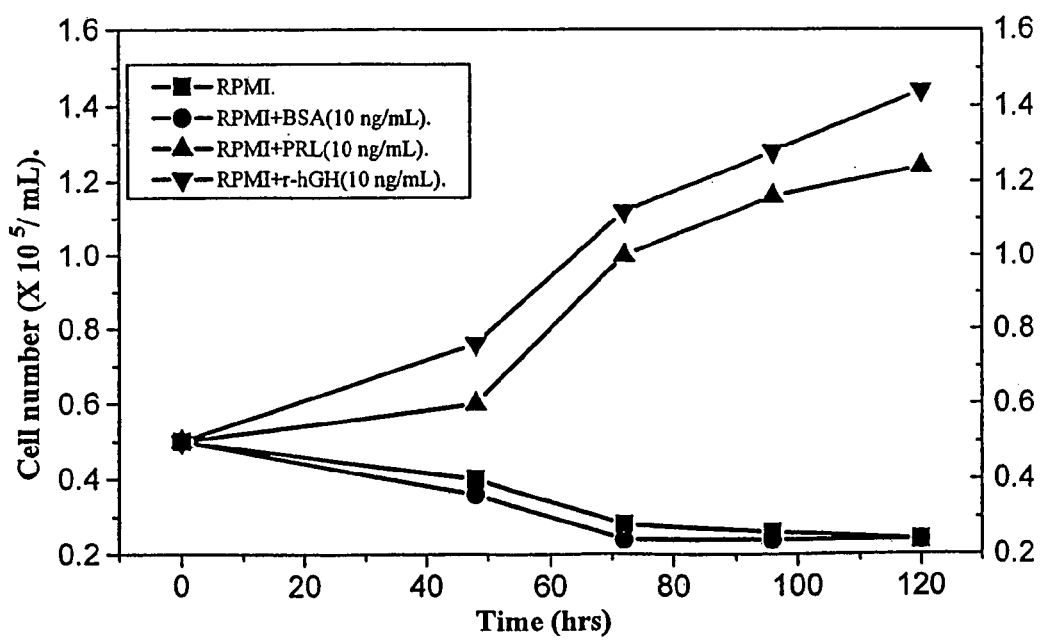

FIG. 5: shows growth kinetics of Nb2 cells in presence of recombinant human growth hormone.

EXAMPLE 1

Improved Recovery of Recombinant Human Growth Hormone From Inclusion Bodies of *E. coli*

Human growth hormone (hGH), a single chain polypeptide containing 191 amino acid residues, apart from stimulating cell growth, plays an important role in variety of metabolic, physiologic and anatomic processes. The protein folds into a four-helix bundle structure with two disulfide bridges, one connecting distant parts of the molecule involving $53^{rd}$ and $165^{th}$ amino acid residues (large loop) and another between residues $182^{nd}$ and $189^{th}$ (small loop). Large scale requirement of r-hGH necessitates its high level expression in *E. coli* as inclusion bodies. However, expression of the protein along with fusion tag and subsequent use of high concentration of chaotropic reagents for solubilization and purification makes the overall process more complex and expensive as they lowers the yield of bioactive r-hGH. Recovery of recombinant human growth hormone from inclusion bodies by solubilization at alkaline pH has also been reported recently. The invention describes a simple and efficient process for the production of bioactive r-hGH from the inclusion bodies of *E. coli*. Solubilization of inclusion body aggregates was carried out using high concentration of β-mercaptoethanol and the solubilized r-hGH was subsequently purified and refolded into bioactive form.

Methods Cloning and Expression of r-hGH:

The synthethic oligonucleotide and HinfI HindIII digested cDNA fragments were inserted into NcoI-HindIII digested pQE-60 expression vector. The construct coding for hGH has just one methionine at the N-terminal end under the control of T5 promoter. The pQE 60 vector carrying the r-hGH coding sequence was then transformed in M15 strain of *Escherichia coli* and was grown in LB or complex medium in presence of both antibiotic markers such as ampicillin (100 μg /ml) and kanamycin (25 μg/ml). The cultures were induced with 1 mM IPTG and were further grown for 4–5 hrs. Expression of r-hGH in the total cell lysate from uninduced and induced cultures was checked by SDS-PAGE.

For large scale production of r-hGH by fed batch, in the form of inclusion bodies, cells were grown in a 3.5 L fermenter in complex medium described in detail in, for example, Mori, H., Yano, T., Kobayashi, T., and Shimizu, S. J. (1979) "High density cultivation of biomass in fed-batch system with DO-Stat", *Chemical Eng. Jpn.* 12, 313–319 and Panda, A. K., Khan, R. H., Appa Rao, K. B. C., and Totey, S. M. (1999) "Kinetics of inclusion body production in batch and high cell density fed-batch culture of *Escherichia coli* expressing ovine growth hormone", *J. Biotechnol.* 75, 161–172, and the initial glucose and yeast extract concentrations were 10 g/L. After 3-h of growth, the cells were grown in fed batch continuous mode with a continuous supply of glucose and yeast extract. The process of fermentation was carried out at 37° C. with both agitation and aeration. Induction with 1 mM IPTG was done at a cell $OD_{600}$ of 60 and was grown for another five hours. Samples were collected at every half-hour during fermentation to check cell growth. Analyses of expression of the fed batch fermentation samples were carried out by SDS-PAGE and was processed for the purification of inclusion bodies.

Isolation and Purification of Inclusion Body:

Cells from the fermenter batch were harvested when the $OD_{600}$ was 60 and were centrifuged at 6000 rpm for 15 minutes. 10 g of cells (wet weight) were taken and was suspended in 50 mL of 50 mM of Tris buffer (pH 8.5) containing 5 mM EDTA and 1 mM PMSF. Homogenization and sonication was carried out methodically to disrupt the cells and was centrifuged at 12000 rpm for 20 minutes to isolate the inclusion bodies from cell debris. It was followed by extensive washings of detergents like sodium salt of deoxycholate in order to remove the *E. coli* membrane proteins. Inclusion bodies were finally washed with MilliQ water to remove the interfering detergents and salts.

Solubilization of Inclusion Body:

To preserve the secondary structure of r-hGH protein while solubilizing the inclusion bodies, strong denaturants like 8 M-urea and 6 M-guanidine hydrochloride were avoided. Solubilization was carried out using a novel protocol where Tris buffer at pH 8.5 contained high concentrations of β-mercaptoethanol in combination with 2 M Urea to improve the solubility levels of inclusion bodies of r-hGH.

Effect of β-mercaptoethanol on the Solubility of inclusion body: To determine the effect of p mercaptoethanol on solubility of the r-hGH, inclusion bodies were solubilized at different concentrations of β mercaptoethanol ranging from 1 M–8 M. Tris-HCl buffer (50 mM) was used and ionic strength and pH of Tris was kept constant with the pH adjusted to 8.5. In all cases, a fixed amount of inclusion bodies was solubilized at a given pH. The percent solubilization was calculated from turbidity measurement at OD450 the resulting solutions and it was further spinned at 12,000 rpm for 15 minutes at 4° C. to estimate it's protein concentration at OD of 280.

Effect of beta mercaptoethanol and urea on the solubility of inclusion body: To determine the synergistic effect of both β-mercaptoethanol and urea on solubility of r-hGH was studied comprehensively. Inclusion bodies of r-hGH were solubilized in different concentrations of β-mercaptoethanol concentrations keeping the concentration of urea constant (2 M) and also a fixed amount of inclusion bodies was taken for the same. The concentration of the former was varied from 1 M–8 M. Protein solution was measured at OD of 450 and OD at 280 to determine the extent of protein solubilization in then above buffer. The effect of β-mercaptoethanol concentration on the solubility of r-hGH inclusion bodies are presented in Table 1.

As shown in Table 1, the solubilization of protein increases with the increase in the concentration of β-Mercaptoethanol and decreases the urea concentration. The maximum solubility is achieved when the concentration of β-Mercaptoethanol is 6 M and the concentration of urea is 2 M.

TABLE 1

| Se. No. | β-Me Conc. (M) | Urea Conc. (M) | Amount of IB taken in mg. | $OD_{450}$ | r-hGH solubility (%) |
|---|---|---|---|---|---|
| 1 | 1 | 1 | 5 | 0.3730 | 6.7 |
| 2 | 1 | 2 | 5 | 0.3150 | 21.2 |
| 3 | 1 | 4 | 5 | 0.2151 | 46.2 |
| 4 | 1 | 6 | 5 | 0.1090 | 72.7 |
| 5 | 2 | 1 | 5 | 0.3418 | 14.5 |
| 6 | 2 | 2 | 5 | 0.3171 | 20.7 |
| 7 | 2 | 4 | 5 | 0.1692 | 57.7 |
| 8 | 2 | 6 | 5 | 0.0452 | 88.7 |
| 9 | 4 | 1 | 5 | 0.0761 | 82.2 |
| 10 | 4 | 2 | 5 | 0.0891 | 77.7 |
| 11 | 4 | 4 | 5 | 0.0205 | 94.9 |
| 12 | 4 | 6 | 5 | 0.0130 | 96.7 |
| 13 | 6 | 1 | 5 | 0.0203 | 95.0 |
| 14 | 6 | 2 | 5 | 0.0104 | 97.4 |
| 15 | 6 | 4 | 5 | 0.0097 | 97.6 |
| 16 | 6 | 6 | 5 | 0.0145 | 96.4 |
| 17 | 8 | 1 | 5 | 0.0104 | 97.4 |
| 18 | 8 | 2 | 5 | 0.0074 | 98.1 |
| 19 | 8 | 4 | 5 | 0.0108 | 97.3 |

Purification of Recombinant Human Growth Hormone:

Solubilization of Inclusion body: *E. coli* cells expressing human growth hormone were lysed by sonication and the pellet containing inclusion bodies were separated by high speed centrifugation. Inclusion bodies of r-hGH was solubilized in 6M β-Mercaptoethanol with 2 M urea. To a homogeneous mixture of inclusion bodies in Tris buffer pH 8.5, 2 M urea and 6 M β-Mercaptoethanol was added to a total volume 10 ml solubilized solution. Protein concentration was around 10 mg/ml. The solubilized r-hGH was centrifuged at 12,000 rpm for 20 minutes at 4° C. The solubilized supernatant was carefully separated from the pellet and used for subsequent refolding and purification Refolding of r-hGH: Recombinant hGH after solubilization by slow pulsatile dilution in ice cold Tris buffer (pH 8.5) containing 0.5 mM EDTA, 2M urea, 10% sucrose, 10% glycerol, 1 mM PMSF kept under constant stirring. To ice cold refolding buffer (90 mL volume) solubilized supernatant was added drop wise manner. In 100 ml of the refolding buffer around 50 mg of the protein could be refolded. Refolded protein was then dialysed against the same refolding buffer in order to remove excess β-mercaptoethanol in a 10 kDa dialysis membrane. Two changes of dialysis was given and it was allowed to undergo air oxidation to aid in the formation of proper disulfide bridge formation.

Purifcation of r-hGH by anion exchange chromatography: The refolded and dialysed r-hGH was loaded on to a pre-equilibrated Q-Sepharose column with a 50 mM Tris, 0.5 mM EDTA, 2M urea, 5% sucrose and 10% glycerol, 1 mM PMSF pH 8.5 at a minimal flow rate of 1 ml/min. Elution was carried out in a linear continuous gradient with the sodium chloride (0 to 0.5 M). Recombinant human growth hormone elutes at conductivity of 8–15 ms/Cm. Elutes of the peak containing human growth hormone was dialysed in order to remove urea, and glycerol. Lyophilization was carried out and the lyophilized protein was reconstituted in 5 ml of buffer and loaded on a gel filtration column (Sephacryl 100). Final purification of recombinant human growth hormone was carried out using gel filtration chromatography which separated the high molecular weight dimmers from the monomer. The pure human growth hormone from the gel filtration column was dialysed and lyophilized for further use.

Characterization of Recombinant Human Growth Hormone:

Purified human growth hormone was characterized by SDS-PAGE and western blotting to authenticate the purity. Further physicochemical and biological assays were carried out to prove the existence of native like conformation of the refolded protein.

Circular Dichroism (CD) Spectroscopy: CD spectra were obtained using a Jasco-700 spectropolarimeter at 25° C. in their respective buffer solutions. The cuvette path length was 1 mm for far-UV region measurements. Each sample was scanned five times, and the averaged spectra were plotted. CD spectra of refolded recombinant human growth hormone were taken to establish the transition curves for r-hGH.

Spectrofluorometric Analysis: Fluorescence spectra of the recombinant was recorded at room temperature with a Shimadzu spectrofluorometer. The spectra were measured at an excitation wavelength of 280 nm. The bandwidth for excitation and emission was 5 nm.

Bioactivity Assay: The biological activity of r-hGH was determined by its growth—promoting action on rat Nb2 lymphoma cell lines. Commercially available recombinant human growth hormone form Boehringer Mannheim was used as standard. The Nb2 cell lines were maintained in RPMI medium supplemented with 10% FBS and 10% HS. Quiescent Nb2 cells arrested at the $G_0/G_1$ phases were prepared by incubating cells in RPMI supplemented with 1% FBS and 10% HS. To initiate cellular proliferation, different concentrations (1–25 ng/ml) each of BSA, commercial hGH or r-hGH were added to the culture medium. The assay was set in a 96 well flat bottom culture plates using RPMI as control. Growth promoting activity was evaluated by counting the number of cells every 24 h for 5 days. Experiments were carried out in triplicate under atmospheric conditions with 5% $CO_2$ at 37° C.

Results:

Expression of r-hGH and its Isolation as Pure Inclusion Bodies:

Transformed *E. coli* cells were grown in fed-batch fermentation process to produce large quantities r-hGH. Culture at cell OD of 60 (28 g/L dry cell weight) was induced with 1 mM IPTG grown for another 5 hrs and the batch was terminated at a cell OD of 80 (FIGS. 1(A and B)). As shown in FIG. 1A, at $OD_{600}$ of 60, the cells were induced with 1 mM IPTG, and grown for 5 hours. A maximum of 2 g/L of r-hGH was expressed as inclusion bodies in 12 hrs of fed-batch fermentation. Expression of r-hGH plateaued after 4 hrs of IPTG induction and the level of r-hGH expression was around 13% of the total cellular protein. As shown in FIG. 1B, cells were lysed and proteins were separated in a 12% SDS-PAGE gel. The molecular weight markers are 14, 21, 30 44, 66 and 90 KDa . Lanes-1, Low Molecular Weight Marker Lanes 2–5 induced samples (induction carried out with imM IPTG), Lanes-6–9 uninduced samples. Most of the cellular proteins were separated from inclusion bodies during the processing of isolation of inclusion bodies. It was seen that maximum removal of the contaminating cellular proteins was achieved by washing the inclusion bodies with help of detergents such as sodium salt of deoxycholate. At the end of the washing, the inclusion bodies contain >95% of r-hGH, the majority in the form of a monomer around 22 kDa along with some higher molecular weight aggregates (near 44 kDa) and immunoblotting of the same indicated the purity of the inclusion body preparation (data not shown). Inclusion bodies thus obtained were used directly for solubilization and refolding.

Solubilization of Inclusion Bodies Using 6 M βMercaptoethanol:

Purified r-hGH inclusion bodies were solubilized in 50 mM Tris buffer at pH 8.5 containing 0.5 mM EDTA, 2 M urea, 6 M βmercaptoethanol, 10% glycerol, 1 mM PMSF. Urea at 2 M level was contributory in improving the solubility of r-hGH and was found to be sufficient to disrupt the hydrophobic interactions. More than 100 mg of inclusion body protein could be completely solubilized in 10 ml above solubilization buffer. The solubilized prteins were separated by high speed centrifuge and processed further for refolding and purification at a remarkably high level was used to provide a highly reducing environment Solubility of r-hGH was increased in a synergistic way using the combination of β-mercaptoethanol along with 2 M urea.

In vitro refolding of the solubilized r-hGH was carried out by pulsatile renaturation in order to increase the overall yield of the bioactive r-hGH. The ice cold refolding buffer contained 50 mM Tris (pH 8.5), 0.5 mM EDTA, 2 M urea, 10% glycerol, imM PMSF to which the solubilized protein was added in pulses at regular intervals. Refolded r-hGH was then subjected to dialysis to remove β-mercaptoethanol whose concentration decreased due to dilution (10×) ie 0.6 M. By giving three dialyis changes the concentration of β-mercaptoethanol was further reduced <6 mM which was negligible enough to load onto an anion exchange column for it's further purification.

Purification of r-hGH: Prior to loading the dialysed r-hGH on to the Q Sepharose column, it was pre-equilibrated with refolding buffer with the addition of 5% sucrose. Elution was carried out by linear continuous gradient 0–0.5 M NaCl gradient (FIG. 2). As shown in FIG. 2, recombinant-hGH solubilized and refolded after dialysis was loaded on the column. Flow rate was 1 mmin. Peaks eluted in NaCl gradient (1 and 2) were used for r-hGH analysis. It was found, that the monomer got eluted between conductivity of 8–14 mS/cm and that of monomer and the dimer got eluted between 15–32 mS/cm. Bands showing a single band on SDS PAGE were pooled and dialysed in presence of 0.1% sucrose to remove urea (FIG. 3). In FIG. 3, Lane 1 corresponds to Ion Exchange Protein load, Lane 2. Molecular weight marker, lanes 3–7 correspond to elute fractions of peak 1. Lanes 8–9 corresponds to elute fractions of peak 2. The peak fraction were lyophilised after dialysis and further purified using Sephacryl-100 column gel filtration chromatography. Pure recombinant human growth hormone coming out of Sephacryl-100 column was lyophilized and characterized. More than 50 mg of pure human growth hormone was recovered from 100 mg of crude inclusion body protein using the above procedure.

Authenticity of the purified r-hGH was further confirmed from the N-terminal analysis of r-hGH and from spectroscopic analysis. UV spectrum of the purified r-hGH showed an absorbance maxima at 276.8 nm, and a shoulder at 283 nm, which was comparable to that of native human growth hormone. The fluorescence spectrum of refolded r-hGH was found to be identical to the native hGH which gave a peak at 340 nm The molar extinction coefficient of pure r-hGH was found to be 18,800 $M^{-1}$ $cm^{-1}$ which is very close to the reported value of 18,890 $M^{-1}$ $cm^{-1}$ for native hGH. The CD spectrum of the refolded r-hGH was similar to that of the native protein (FIG. 4). In this FIG. 4, which is a CD spectroscopy of the refolded r-hGH was carried out at a wavelength of 292 nm. A and B are the CD spectra of refolded r-hGH. The refolded r-hGH showed characteristics of a helix have peak minimum at 210 and 220, a pattern similar to the native hGH.

Growth kinetics of prolactin-dependent Nb2 lymphoma cell line was monitored to evaluate the bioactivity of purified r-hGH. Addition of prolactin, commercial hGH and r-hGH promoted growth of Nb2 cells arrested at $G_0/G_1$ phase by serum deprivation. Growth of Nb2 cells in presence of different concentrations of r-hGH was found to be comparable to that observed for the commercial hGH (FIG. 5). As shown in FIG. 5, Bioactivity of r-hGH was carried out using Nb2 cell line to study the growth promoting activity. Cell growth was arrested by serum deprivation and different concentrations of r-hGH or commercially available hGH or Bovine Serum Albumin in RPMI medium for activation of cell growth. Cell growth was monitored by counting the number of cells on different days. Cell concentrations achieved at 96 h after activation are presented to compare the bioactivity of r-hGH with that of commercially available hGH. No growth stimulation was observed in the presence of BSA which was used as a negative control. This indicated the bioactivity of the refolded protein. Bioactivity assay further confirmed that by solubilization of inclusion body proteins using high concentration of β-Mercaptoethanol it is possible to refold the denatured protein from the inclusion bodies in to native conformation. Such process is simple and helps in improved recovery of the bioactive protein. Such solubilization protocol can be applied to recover bioactive protein from the inclusion bodies of *E. coli*.

EXAMPLE 2

Enolse expressed as inclusion bodies in *E. coli* was solubilized and refolded in to bioactive form using this method. Fed-batch fermentation of *E. coli* resulted in production of 1 g/L of recombinant enolase as inclusion bodies. The denatured recombinant enolase in the form of inclusion bodies were isolated and purified from the cell by lysis and centrifugation. The inclusion body pellet was dissolved in 6 M β-Mercaptoethanol in presence 2 M urea solution. The solubilized enolase was separated by high speed centrifuge. Solubulized protein was dialysed in presence of 2 M urea to remove β-Mercaptoethanol. The protein was then recovered by conventional methods.

EXAMPLE 3

Polyketide synthase (PKS) of *Mycobacterium tuberculosis* was expressed as inclusion bodies in *E. coli*. The recombinant PKS was solubilized and refolded in to bioactive form using this method. Fed-batch fermentation of *E. coli* resulted in production of 2 g/L of recombinant PKS as inclusion bodies. The denatured recombinant PKS in the form of inclusion bodies were isolated and purified from the cell by lysis and centrifugation. He inclusion body pellet was dissolved in 6 M β-Mercaptoethanol in presence 2 M urea solution. The solubilized recombinant PKS was separated by high speed centrifuge. Solubulized protein was dialysed in presence of 2 M urea to remove β-Mercaptoethanol. The protein was then recovered by conventional methods.

Similar solubilization protocol was using β-mercaptoethanol with low molar urea has been successfully used for the solubilization of proteins aggregates formed during high level expression of recombinant proteins. Examples of proteins solubilized are recombinant bonnet monkey zona pellucida protein expressed as aggregates in insect cell culture system. The solubulized aggregates could be then refolded using standard refolding procedure. Complex membrane proteins when expressed even using eukaryotic expression system results in accumulation as inclusion bodies. As the above solubilization process is based on disruption of hydrophobic interaction and disulfide bond formation, such solubilizatin process can thus be used to solubilized protein aggregated formed during high level expression of recombinant proteins such as growth factors, interferrons, interleukins, hormones and antibody fragments.

ADVANTAGES high recovery of bioactive protein,
low aggregation during refolding of the inclusion body proteins which helps in improving the overall recovery of bioactive protein from the inclusion body stage.
process useful for solubilization of recombinant protein aggregates specifically formed during high level expression in host cells.
solubilization of inclusion body protein aggregates without using high molar concentration of chaotropic solvent which completely unfold the protein molecules in to random coli structure.
selective solubilization of heterologous protein expressed as inclusion bodies in *E. coli*.
mild solubilization procedure which does not result in massive aggregation of the solubilized protein during the removal of the solubilization agent.
solubilization protocol of inclusion body aggregates which help in better recovery of the bioactive protein in comparison to solubilization using high molar concentration of chaotropic agents.
process protects the native like secondary structure of the inclusion body proteins.

The invention claimed is:

1. A process for solubilization of a growth hormone protein in the form of inclusion bodies from a host cell and its subsequent refolding and recovery into bioactive form, the process comprising:
   (a) providing a host cell chosen from *Escherichia coli* or insect cells incorporating an insoluble synthesized or expressed growth hormone protein in the form of an inclusion body,
   (b) isolating the inclusion body and treating with a denaturating solution consisting of a mercaptoethanol solvent at a concentration of 6–8 M and urea at a concentration of 1–2 M to solubilize the protein aggregates and obtain solubilized protein, and (c) refolding the solubilized protein by treatment with a refolding buffer of pH 8.5 to obtain a protein in its bioactive form.

2. A process as claimed in claim 1, wherein the growth hormone is selected from human growth hormone, porcine growth hormone and bovine growth hormone.

3. A process of solubilization of growth hormone from a host cell chosen from *Escherichia coli* or insect cells, the process comprising disrupting both hydrophobic interaction and disulfide bond formation of the proteins resulting in solubilization of the protein aggregates using high concentration of about 6–8 M of a mercaptoethanol solvent in the presence of 2 M urea solution.

4. A process as claimed in claim 1 where the subsequent removal of the solubilizing agents results in renaturation of the recombinant protein, and pulsatile dilution of the solubilizing agents results in renaturation of protein.

5. A process as claimed in claim 1 wherein refolding of the solubilized protein is carried out at a protein concentration of around 1 mg/ml.

6. A process as claimed in claim 4 wherein pulsatile dilution of the solubilizing agents results in renaturation of protein.

7. A process as claimed in claim 1 wherein the buffer includes 50 Mn of a tris (hydroxymethyl) aminomethane buffer.

8. A process as claimed in claim 1 wherein the buffer includes 10% glycerol.

9. A process as claimed in claim 1 wherein the buffer includes 5% sucrose.

10. A process as set forth in claim 1 wherein the buffer includes 2 M of urea.

* * * * *